(12) United States Patent
Ghimire et al.

(10) Patent No.: US 11,948,389 B2
(45) Date of Patent: Apr. 2, 2024

(54) SYSTEMS AND METHODS FOR AUTOMATIC DETECTION OF ANATOMICAL SITES FROM TOMOGRAPHIC IMAGES

(71) Applicants: Kanchan Ghimire, Arlington, VA (US); Quan Chen, Lexington, KY (US); Xue Feng, Lexington, KY (US)

(72) Inventors: Kanchan Ghimire, Arlington, VA (US); Quan Chen, Lexington, KY (US); Xue Feng, Lexington, KY (US)

(*) Notice: Subject to any disclaimer, the term of this patent is extended or adjusted under 35 U.S.C. 154(b) by 265 days.

(21) Appl. No.: 17/693,272

(22) Filed: Mar. 11, 2022

(65) Prior Publication Data

US 2023/0316796 A1 Oct. 5, 2023

(51) Int. Cl.
*G06V 40/10* (2022.01)
*G06V 10/26* (2022.01)
(Continued)

(52) U.S. Cl.
CPC ............ *G06V 40/10* (2022.01); *G06V 10/267* (2022.01); *G06V 10/273* (2022.01); *G06V 10/28* (2022.01);
(Continued)

(58) Field of Classification Search
CPC .... G06V 40/10; G06V 10/267; G06V 10/273; G06V 10/28; G06V 10/34; G06V 10/457;
(Continued)

(56) References Cited

U.S. PATENT DOCUMENTS

2010/0231605 A1\* 9/2010 Moriya .................. G06T 19/00
345/619
2011/0257919 A1\* 10/2011 Reiner .................... G06F 16/51
702/81

(Continued)

FOREIGN PATENT DOCUMENTS

WO WO-2022164374 A1 \* 8/2022

OTHER PUBLICATIONS

Whole-body Computed Tomography Versus Dual Energy X-ray Absorptiometry for Assessing Heterotopic Ossification in Fibrodysplasia Ossificans Progressiva—2021 (Year: 2021).\*

(Continued)

*Primary Examiner* — Nizar N Sivji (57) ABSTRACT

The present disclosure relates to a method and apparatus for automatic detection of anatomical sites from tomographic images. The method includes: receiving 3D images obtained by a CT or an MRI system, transforming the images to the DICOM standard patient-based coordinate system, pre-processing the images to have normalized intensity values based on their modality, performing body segmentation, cropping the images to remove excess areas outside the body, and detecting different anatomical sites including head and neck, thorax, abdomen, male pelvis and female pelvis, wherein the step of detecting different anatomical sites comprises: performing slice-level analyses on 2D axial slices to detect the head and neck region using dimensional measurement thresholds based on human anatomy, calculating lung ratios on axial slices to find if lungs are present, determining whether 3D images with lungs present span over the thoracic region, abdomen region, or both, conducting 2D connectivity analyses on axial slices to detect the pelvis region if two separate leg regions are found and differentiating detected pelvis regions as either male pelvis or female pelvis regions based on human anatomy.

17 Claims, 5 Drawing Sheets

(51) Int. Cl.
 G06V 10/28 (2022.01)
 G06V 10/34 (2022.01)
 G06V 10/44 (2022.01)
 G16H 30/20 (2018.01)
 G16H 30/40 (2018.01)

(52) U.S. Cl.
 CPC ............ *G06V 10/34* (2022.01); *G06V 10/457* (2022.01); *G16H 30/20* (2018.01); *G16H 30/40* (2018.01); *G06V 2201/031* (2022.01)

(58) Field of Classification Search
 CPC ... G06V 2201/031; G16H 30/20; G16H 30/40
 See application file for complete search history.

(56) References Cited

U.S. PATENT DOCUMENTS

2020/0037962 A1* 2/2020 Shanbhag .............. A61B 5/055
2020/0327661 A1* 10/2020 Oved .................... G16H 30/20

OTHER PUBLICATIONS

Artificial intelligence radiotherapy planning: automatic segmentation of human organs in CT images based on a modified convolution neural network—2022 (Year: 2022).*
Quality of DICOM header information for image categorization—2022 (Year: 2022).*
Extra-cardiac findings in cardiovascular magnetic resonance: what the imaging cardiologist needs to know—2016 (Year: 2016).*
Non-Contrast-Enhanced Whole-Body Magnetic Resonance Imaging in the General Population: The Incidence of Abnormal Findings in Patients 50 Years Old and Younger Compared to Older Subjects—2014 (Year: 2014).*
Development of a virtual source model for Monte Carlo-based independent dose calculation for varian linac—2021 (Year: 2021).*
Automatic contouring system for cervical cancer using convolutional neural Networks—2020 (Year: 2020).*
Development, validation, and pilot MRI safety study of a high-resolution, open source, whole body pediatric numerical simulation model—2021 (Year: 2021).*

* cited by examiner

HeadNeck ☐
Thorax ▨
Abdomen ▨
MalePelvis ☐
FemalePelvis ☐

SYSTEMS AND METHODS FOR AUTOMATIC DETECTION OF ANATOMICAL SITES FROM TOMOGRAPHIC IMAGES

STATEMENT OF GOVERNMENT INTEREST

This invention was made with government support under Grant No. R44CA254844 awarded by The National Institute of Health. The government has certain rights in the invention.

CROSS-REFERENCE TO RELATED APPLICATION

Not applicable.

FIELD

This disclosure relates to computed tomography (CT) and magnetic resonance imaging (MRI) operations that develop and validate a framework for the automatic detection of anatomical sites.

BACKGROUND

Image processing, a method for extracting useful information from an image, plays a significant role in many medical imaging applications. The automatic detection of anatomical sites supports various radiological products by performing an automated check of whether the provided tomographic images span the target region-of-interest. While there are some tools and software available to perform image processing, these tools tend to fail for specific tasks such as detecting different anatomical sites. Moreover, the detection of anatomical sites is hindered by varying image modalities and imaging protocols, both of which affect image intensity values. Therefore, a generic method for the detection of anatomical sites that can handle tomographic images of different modalities is needed.

SUMMARY

Examples of the present disclosure provide a method for the automatic detection of anatomical sites from tomographic images using rule-based image processing algorithms.

According to a first aspect of the present disclosure, a computer-implemented method for the automatic detection of anatomical sites. The method may include: receiving 3D images obtained by a CT or an MRI system, transforming the images to the DICOM standard patient-based coordinate system, pre-processing the images to have normalized intensity values based on their modality, performing body segmentation, cropping the images to remove excess areas outside the body, and detecting different anatomical sites including head and neck, thorax, abdomen, male pelvis and female pelvis, wherein the step of detecting different anatomical sites comprises: performing slice-level analyses on 2D axial slices to detect the head and neck region using dimensional measurement thresholds based on human anatomy, calculating lung ratios on axial slices to find if lungs are present, determining whether 3D images with lungs present span over the thoracic region, abdomen region, or both, conducting 2D connectivity analyses on axial slices to detect the pelvis region if two separate leg regions are found and differentiating detected pelvis regions as either male pelvis or female pelvis regions based on human anatomy.

According to a second aspect of the present disclosure, an apparatus for automatic detection of anatomical sites. The apparatus may include one or more processors, a display, and a non-transitory computer-readable memory storing instructions executable by the one or more processors. Wherein the instructions are configured to receive 3D images obtained by a CT or an MRI system, transform the images to the DICOM standard patient-based coordinate system, pre-process the images to have normalized intensity values based on their modality, perform body segmentation, crop the images to remove excess areas outside the body, and detect different anatomical sites including head and neck, thorax, abdomen, male pelvis and female pelvis, wherein the step to detect different anatomical sites includes instructions that are configured to: perform slice-level analyses on 2D axial slices to detect the head and neck region using dimensional measurement thresholds based on human anatomy, calculate lung ratios on axial slices to find if lungs are present, determine whether 3D images with lungs present span over the thoracic region, abdomen region, or both, conduct 2D connectivity analyses on axial slices to detect the pelvis region if two separate leg regions are found and differentiate detected pelvis regions as either male pelvis or female pelvis regions based on human anatomy.

According to a third aspect of an example of the present disclosure, a non-transitory computer-readable storage medium having stored therein instructions is provided. When the instructions are executed by one or more processors of the apparatus, the instructions cause the apparatus to receive 3D images obtained by a CT or an MRI system, transform the images to the DICOM standard patient-based coordinate system, pre-process the images to have normalized intensity values based on their modality, perform body segmentation, crop the images to remove excess areas outside the body, and detect different anatomical sites including head and neck, thorax, abdomen, male pelvis and female pelvis, wherein the step to detect different anatomical sites includes instructions that are configured to: perform slice-level analyses on 2D axial slices to detect the head and neck region using dimensional measurement thresholds based on human anatomy, calculate lung ratios on axial slices to find if lungs are present, determine whether 3D images with lungs present span over the thoracic region, abdomen region, or both, conduct 2D connectivity analyses on axial slices to detect the pelvis region if two separate leg regions are found and differentiate detected pelvis regions as either male pelvis or female pelvis regions based on human anatomy.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 3 is an example of the algorithm's results shown on 3D CT images for the automatic detection of anatomical sites (head and neck region), according to an example of the present disclosure.

FIG. 4 is an example implementation of the algorithm for the automatic detection of anatomical sites, according to an example of the present disclosure.

FIG. 5 is an example of the algorithm's results shown on 3D CT images for the automatic detection of anatomical sites (pelvis region), according to an example of the present disclosure.

DETAILED DESCRIPTION

Reference will be made in detail to example embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms "a," "an," and "the" are intended to include the plural forms as well, unless the context clearly indicates otherwise. It shall also be understood that the term "and/or" used herein is intended to signify and include any or all possible combinations of one or more of the associated listed items.

It shall be understood that, although the terms "first," "second," "third," etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

The present disclosure related to a detection framework to automatically detect different anatomical sites from CT or MRI images.

Figure 1:
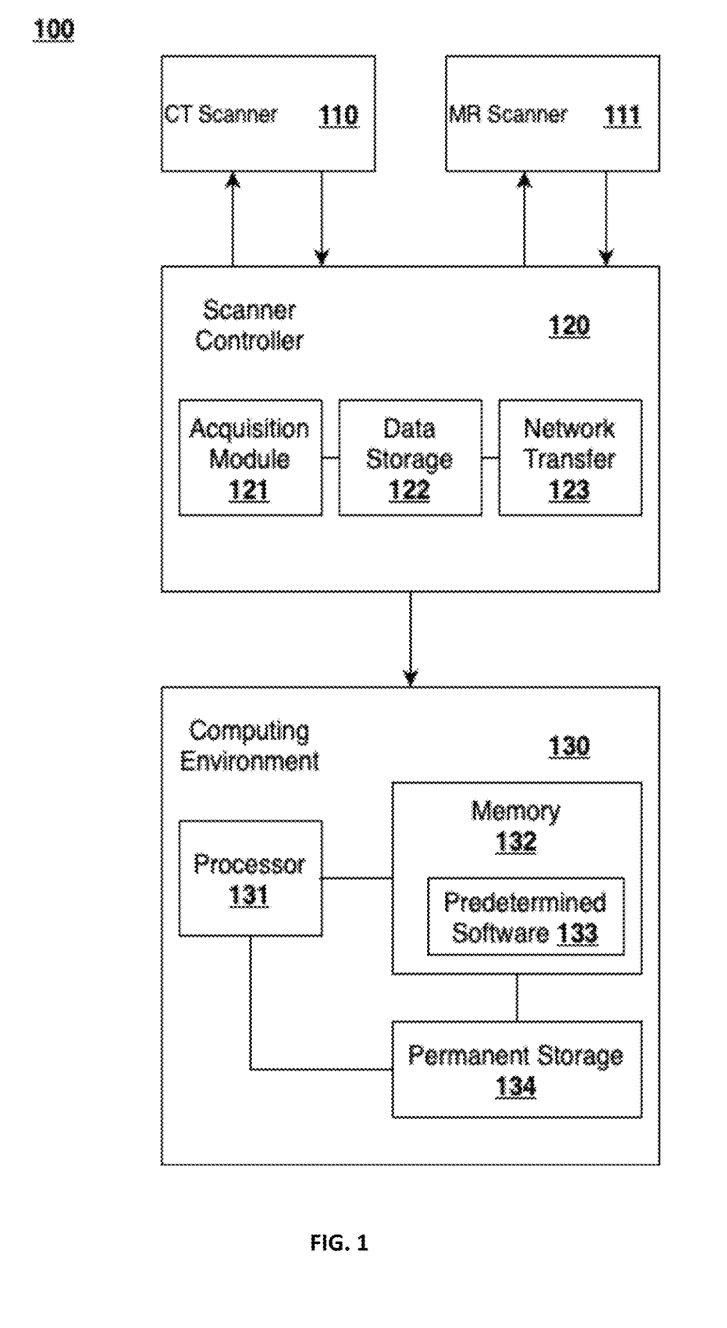
FIG. 1 is a system diagram of CT/MRI scanner, controller and computing environment illustrating an operating environment capable of implementing aspects of the present disclosure.

FIG. 1 shows a system diagram of CT scanner 110 or magnetic resonance (MR) scanner 111, controller 120, and computing environment 130. The CT scanner 110 or MR scanner 111 is used to obtain CT/MRI images covering the body region of a subject and is controlled by the scanner controller 120. The scanner controller 120 contains the acquisition module 121 that drives the CT scanner 110 or MR scanner 111, the data storage module 122 that stores the CT/MRI images of different subjects, and the network transfer module 123 that sends the CT/MRI images to another computing environment 130. The computing environment 130 contains processor 131, memory 132, and permanent storage 135 to perform given directions. In executing the directions, the predetermined software 133 is loaded into memory 132 and is executed by processor 131 to yield the desired output.

The processing component 120 typically controls overall operations of the computing environment 130, such as the operations associated with display, data acquisition, data communications, and image processing. The processor 131 may include one or more processors to execute instructions to perform all or some of the steps in the above-described methods. Moreover, the processor 131 may include one or more modules which facilitate the interaction between the processor 131 and other components. The processor may be a Central Processing Unit (CPU), a microprocessor, a single chip machine, a graphics processing unit (GPU), or the like. The memory 132 is configured to store various types of data to support the operation of the computing environment 130. The memory 132 may be implemented by using any type of volatile or non-volatile memory devices, or a combination thereof, such as a static random-access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

In an embodiment, the computing environment 130 may be implemented with one or more application specific integrated circuits (ASICs), digital signal processors (DSPs), digital signal processing devices (DSPDs), programmable logic devices (PLDs), field programmable gate arrays (FPGAs), GPUs, controllers, micro-controllers, microprocessors, or other electronic components, for performing the above methods.

The method for automatic detection of different anatomical sites from different tomographic images is programmed as one set of predetermined software 133 and installed on the computing environment 130. When the computing environment 130 receives CT/MRI images from scanner controller 120, the predetermined software 133 is executed to generate the results.

Figure 2:
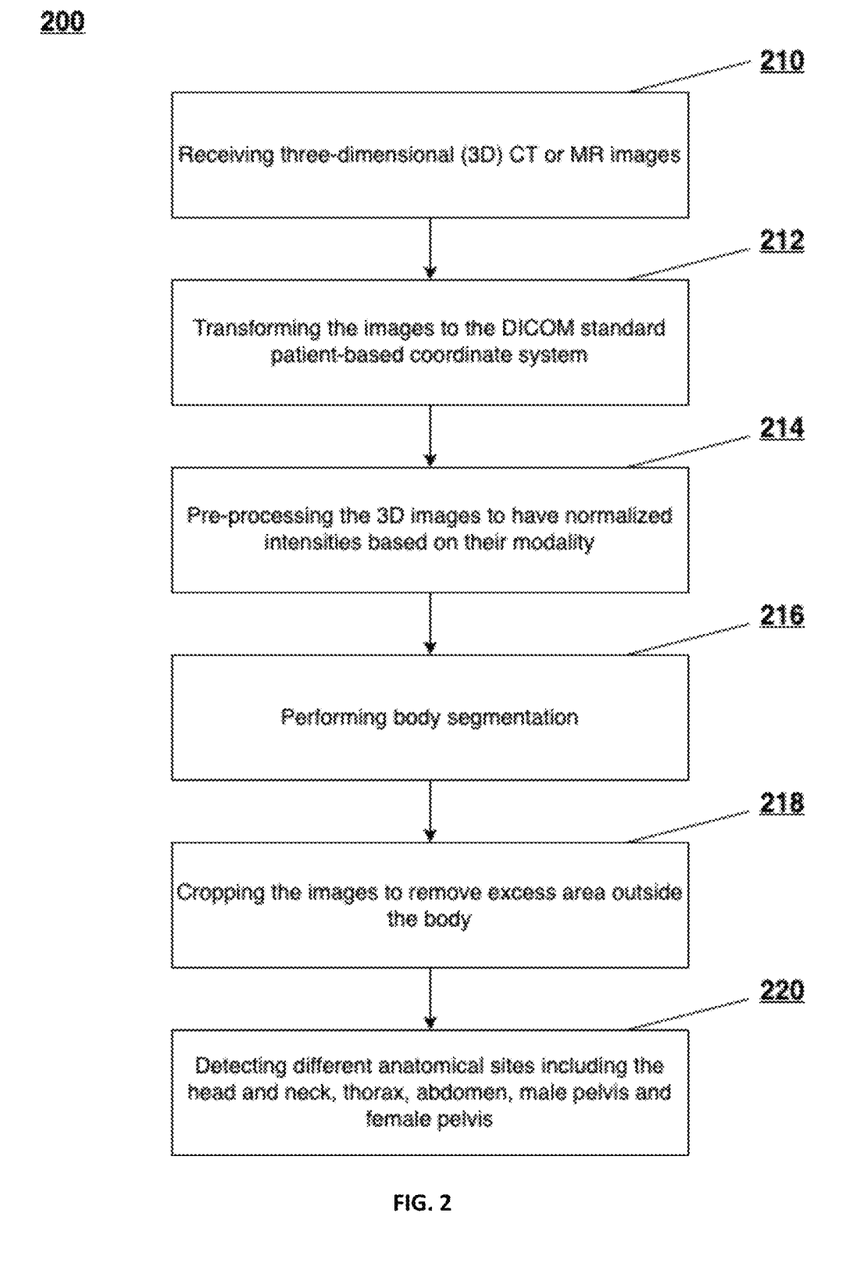
FIG. 2 is a flow chart illustrating a method to automatically detect different anatomical sites, according to an example of the present disclosure.
Figure 3A:
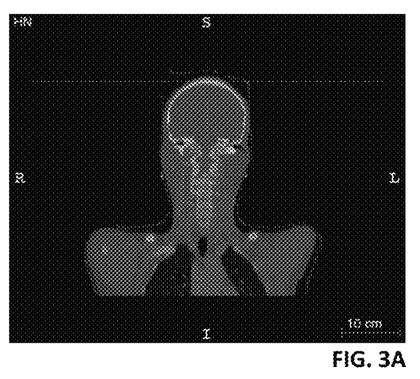
FIG. 3A is a coronal view of a 3D CT image covering the head and neck region, with a horizontal blue line showing the top of the head and neck region as detected by the algorithm.
Figure 3B:
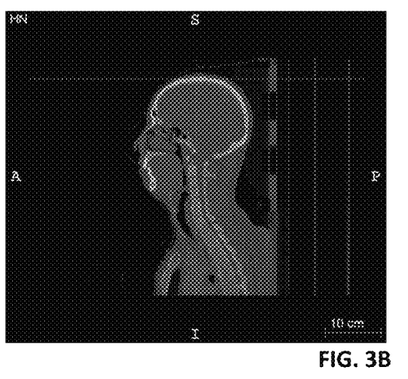
FIG. 3B is a sagittal view of a 3D CT image covering the head and neck region, with a horizontal blue line showing the top of the head and neck region as detected by the algorithm.
Figure 3C:
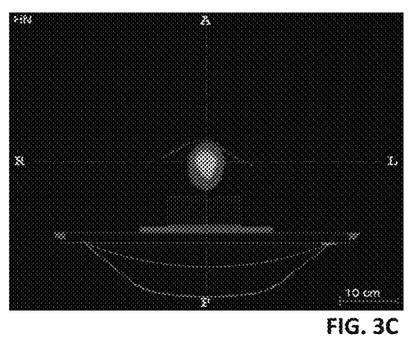
FIG. 3C is an axial view of a 3D CT image covering the head and neck region, which is the top slice of the head and neck region as detected by the algorithm.
Figure 3D:
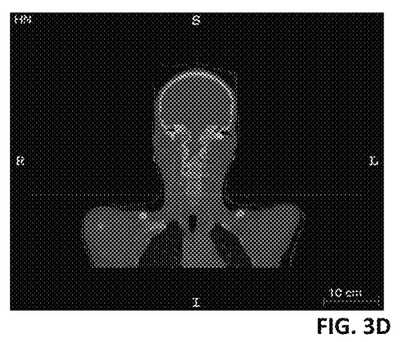
FIG. 3D is a coronal view of a 3D CT image covering the head and neck region, with a horizontal blue line showing the bottom of the head and neck region as detected by the algorithm.
Figure 3E:
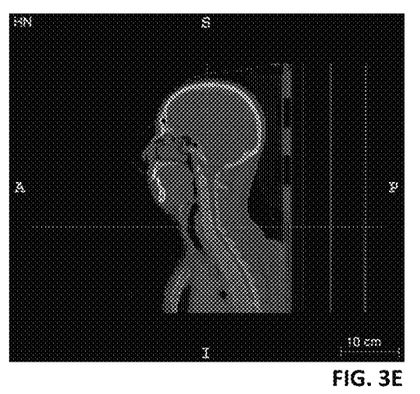
FIG. 3E is a sagittal view of a 3D CT image covering the head and neck region, with a horizontal blue line showing the bottom of the head and neck region as detected by the algorithm.
Figure 3F:
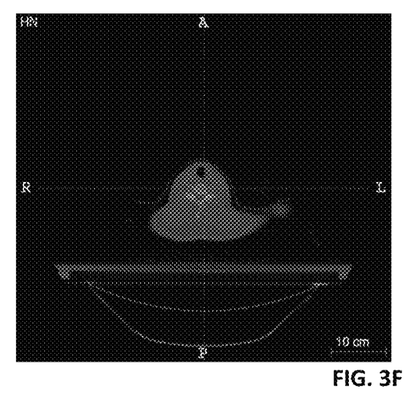
FIG. 3F is an axial view of a 3D CT image covering the head and neck region, which is the bottom slice of the head and neck region as detected by the algorithm.

In step 210, 3D CT/MRI images covering a specific body region are received. FIG. 3A, FIG. 3B, and FIG. 3C show an example of 3D CT images received, where FIG. 3A shows a sagittal view, FIG. 3B shows a coronal view, and FIG. 3C shows an axial view.

In step 212, 3D images are transformed to the DICOM standard patient-based coordinate system. A rotation matrix is computed based on the direction of the acquired 3D images. Then, according to the DICOM standard, the 3D images are transformed to align in all directions: from superior to inferior in the axial direction, right to left in the sagittal direction and anterior to posterior in the coronal direction.

In step 214, 3D images are pre-processed to have normalized intensities to reduce variability within the dataset. The pre-processing steps include intensity cropping and normalization. For CT images, voxel intensity values outside of the range [−1000, 600] Hounsfield units (HU) were set to −1000 and 600, respectively. Similarly, for other modalities, the upper and lower threshold limits were decided based on the $95^{th}$ and $1^{st}$ percentile intensity values. With this, values outside the upper and lower limits were set to those corresponding values. Last, image intensity values were normalized to the range [0, 1].

In step 216, body segmentation is performed. To reduce the computation time for running the body segmentation algorithm, a fast resizing of the images was performed. After resizing, thresholding is applied, where the 3D images' voxels are converted from normalized intensity values to a binary value classifying the voxels as either "foreground" or "background." If a voxel's normalized intensity value is greater than a threshold of 0.15, it is classified as a foreground (part of the body). All other voxels are then classified as background. After thresholding, morphological operations and 3D connectivity analyses are performed to improve the initial body segmentation. Holes within the body segmentation are identified and filled on a 2D slice-by-slice basis via morphological closing. Next, a 3D connectivity analysis is performed. In the connectivity analysis, two voxels are defined as connected when they are neighbors and have the same value. In 3D, voxels can be neighbors either in a 4- or 8-connected sense, where these values refer to the maximum number of orthogonal hops needed to consider a voxel as a neighbor. Voxels with 4-connectivity share a face, whereas voxels with 8-connectivity share only an edge or a vertex. The connectivity analysis identifies all voxels with 8-connectivity and removes non-connected regions.

In step 218, images are reduced in size by cropping the excess areas outside of the body.

In step 220, different anatomical sites including the head and neck, thorax, abdomen, and pelvis are detected. To detect different body regions, the algorithm looks for each of the regions sequentially from superior to inferior. As such, the head and neck regions are the first anatomical sites for which the algorithm searches. Body segmentation assists the detection process such that the body regions are constrained to be within the segmented body. From superior to inferior, a slice-level analysis is performed on axial slices. For each axial slice, morphological erosion is performed to separate the center region (i.e., the head) from noise (i.e., the hands placed on the side of the head during imaging). Then, the left-right dimension is measured in absolute mm to determine if it lies below a threshold of accepted head-neck size (250 mm) based on human anatomy. Once the top of the head and bottom of the neck is determined, the length of the head/neck region is measured in absolute mm. Similar thresholding is implemented to determine whether the head and neck region is present in the 3D images, The length of the average human head and neck region is about 200 mm to 300 mm. As such, if the measured head/neck length is between 100 mm and 320 mm, we consider the head/neck region detected. If the length is less than 100 mm, then the images are potentially not useful in performing any anatomical-based operations for the head/neck region. Similarly, if the length is greater than 320 mm, then an error may be present in either the imaging and/or detection. In this case, the algorithm outputs that the head and neck region is not detected. It is important to note that pixel spacing and slice thickness were accounted for while performing these measurements.

If the head and neck region is detected in the images, the z field-of-view (FOV) is then calculated to find the length of the body (in absolute mm) present in the images. If the length of the body is large enough (>800 mm) to accommodate all the body regions named above, all body regions will be considered detected, and the algorithm will stop looking for new regions. However, if the z-FOV is not large enough to span the entire body, the algorithm will then look to see if it can find the thoracic region. One of the criteria used to detect thoracic region is by looking for the presence of lungs. The algorithm considers this an important anatomical reference while detecting the thoracic region. In both CT and MR images, there is a significant difference in intensity values between the lungs and the rest of the body due to the presence of air in the lungs. As such, the lung ratio on axial slices can be calculated to determine the top and/or end of the lungs. If the images span the whole length of the lungs, the detected region is most likely a thoracic region. However, there are some cases where the abdomen region covers the whole length of the lungs as well.

Figure 4A:
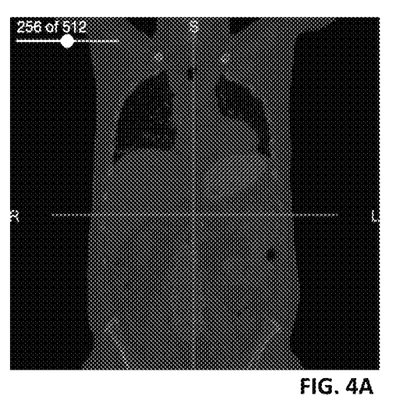
FIG. 4A is a coronal view of a 3D CT image covering the thoracic and abdominal regions.
Figure 4B:
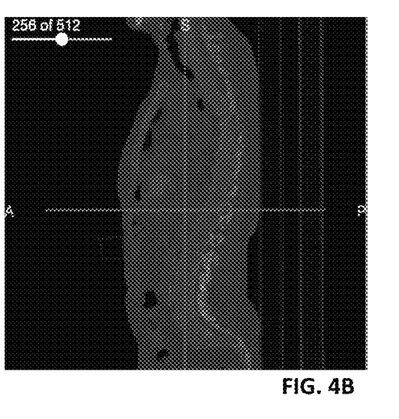
FIG. 4B is a sagittal view of the same 3D CT image as FIG. 3A, covering the thoracic and abdominal regions.
Figure 4C:
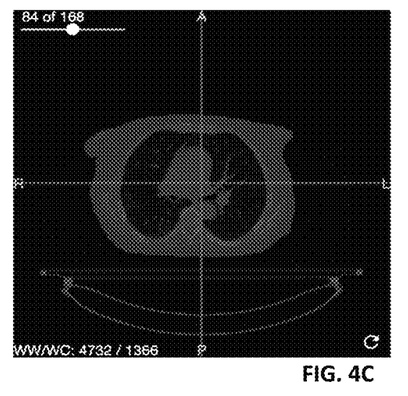
FIG. 4C is an axial view of the lungs from the same 3D CT image as FIG. 3A.
Figure 4D:
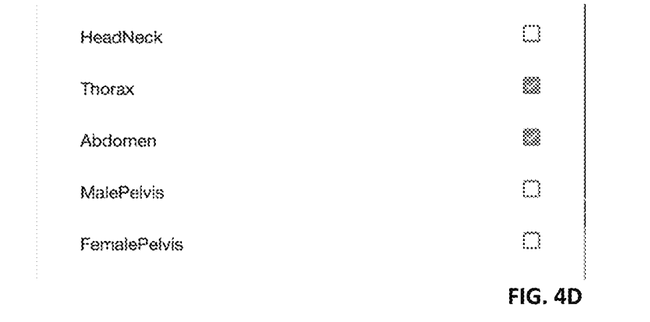
FIG. 4D is the output of the automatic detection algorithm for the 3D CT image shown in FIG. 4A, FIG. 4B, and FIG. 4C that correctly detects the thorax and abdomen body regions.

An additional criterion is used to determine whether the region with lungs should be considered the thoracic or abdomen region. Since the thoracic region covers some regions-of-interest (ROIs) superior to the lungs, images are checked for the presence of the neck using the head-neck detection criteria described above. The neck is considered present if the detected head/neck region spans at least 5 mm in the z-FOV. The thorax region is detected if whole-length lungs and part of the neck are present in the images. If the thorax region is detected and there is a significant z-FOV (>400 mm) below the end of the lungs to cover the abdomen, both the thorax and the abdomen are detected. FIGS. 4A, 4B, and 4C show an example of CT images covering both the thoracic and the abdomen regions. However, if the neck is not present and part of the lungs is present, then the abdomen region is detected in the images. FIG. 4D shows an example algorithm output for the image described by FIGS. 4A and 4B, where the checked-box next to 'Thorax' and 'Abdomen' show that both thoracic and abdomen regions are automatically detected on the given image.

Figure 5A:
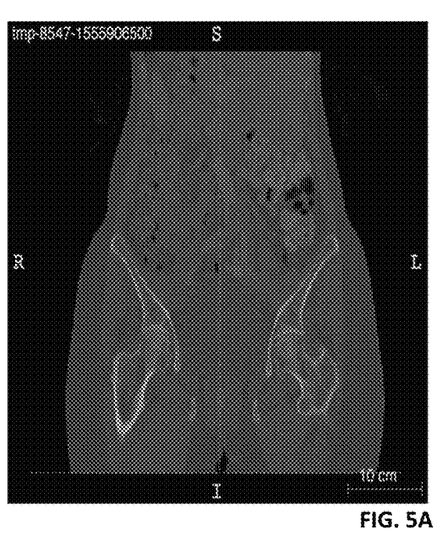
FIG. 5A is a coronal view of a 3D CT image covering the pelvis region, which the algorithm accurately detected as the pelvis region.
Figure 5B:
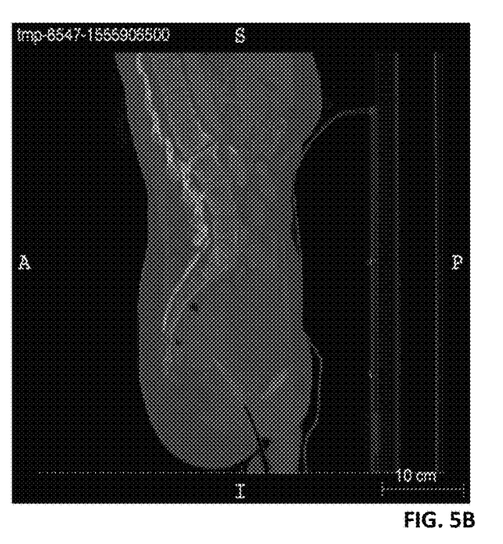
FIG. 5B is a sagittal view of a 3D CT image covering the pelvis region, which the algorithm accurately detected as the pelvis region.
Figure 5C:
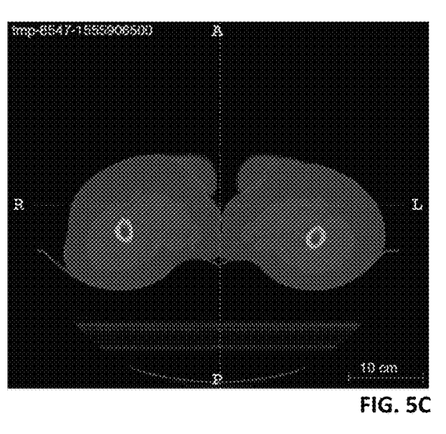
FIG. 5C is an axial view of a 3D CT image covering the pelvis region, which the algorithm accurately detected as the pelvis region; the blue vertical line shows the region that splits after morphological erosion applied by the algorithm and outputs two regions of roughly the same area based on which the algorithm would detect the pelvis region.

After detecting the thoracic and abdomen regions for the image, the algorithm then inspects the image for the pelvis region. Anatomically speaking, the pelvis covers part of the thigh area (thigh split). This fact is used to determine the presence of the pelvis in the image. To begin, morphological erosion is performed on each axial slice to find two distinct leg regions. The top-most (superior) axial slice that has two distinct regions of roughly the same area can be considered as the area where the thigh splits into two legs.

Finally, the pelvis (if detected) is then differentiated between male and female. If the images obtained step 210 contain the patient sex information as either male or female, the algorithm uses this information to classify the pelvis as male and female. However, if the patient's sex information is missing, the algorithm performs further slice-level analysis to determine the gender. Morphological erosion (heavy erosion) of the pelvis is performed on axial slices, and the male pelvis is detected if the 2D connectivity analysis after erosion shows three distinct regions (two legs and one male genital). If the pelvis region is not classified as male, it is then classified as female.

What is claimed is:

1. A computer-implemented method for the automatic detection of anatomical sites using one or more processors, the method comprising:
   receive 3D images obtained by a CT or an MRI system;
   transform the received 3D images to the DICOM standard patient-based coordinate system;
   pre-process the transformed images to normalize intensity values based on the received 3D images obtained by the CT or MRI system;
   perform image segmentation on the pre-processed transformed images to obtain the body mask;
   crop the pre-processed transformed images to remove excess areas outside the segmented body mask;
   wherein anatomical sites consisting of head and neck, thorax, abdomen, male pelvis and female pelvis;
   wherein the step of detecting the anatomical sites comprises:
   create an empty list;
   perform slice-level analyses on 2D axial slices of the pre-processed transformed images to detect the presence of the head and neck region using dimensional measurement thresholds based on human anatomy;
   add the head and neck region in the list,
   if the head and neck region is present;
   perform image segmentation on the pre-processed transformed images to obtain lung mask;
   calculate lung ratios on the 2D axial slices to determine if the lung mask are present in the axial slices;
   determine whether the pre-processed transformed images with lung mask present includes at least one of the thoracic region, abdomen region or at least one of the combination thereof;
   verify presence of neck region to determine the presence of thoracic region or the abdomen region;
   determine the presence of both the thoracic region and the abdomen region,
   if the thoracic region is present and the field-of-view of the pre-processed transformed images in the axial direction is large enough to cover both the thoracic and abdomen regions;
   add the thoracic region or the abdomen region or both in the list,
   if the thoracic region or the abdomen region or both are present;
   determine the presence of pelvis region on the pre-processed transformed images with lung mask present;
   determine the presence of pelvis region on the pre-processed transformed images with no lung mask present by conducting 2D connectivity analysis on the 2D axial slices;
   differentiate detected pelvis region as either male pelvis or female pelvis region based on human anatomy;
   add male pelvis or female pelvis region in the list,
   if the pelvis region is present; and
   output the list of all the detected anatomical sites.

2. The computer-implemented method for the automatic detection of anatomical sites according to claim 1, wherein transform the received 3D images to the DICOM standard patient-based coordinate system comprises:
   transform the received 3D images to be sorted from superior to inferior in the axial direction, right to left in the sagittal direction, and anterior to posterior in the coronal direction.

3. The computer-implemented method for the automatic detection of anatomical sites according to claim 1, wherein pre-process the transformed images to normalize intensity values based on received 3D images obtained by the CT or MRI system comprises:
   receive the 3D images information includes pixel spacing, slice thickness, matrix size, and patient's sex;
   apply lower and upper thresholds on CT image Hounsfield unit (HU) intensities; and
   apply lower and upper thresholds on MRI image intensities using the image intensity percentiles.

4. The computer-implemented method for the automatic detection of the anatomical sites according to claim 1, wherein perform the image segmentation on the pre-processed transformed images to obtain the body mask comprises:
   apply threshold to image intensity;
   perform 3D connectivity analysis to find 3D connected region after applying threshold to image intensity; and
   fill holes to further improve the body mask segmentation.

5. The computer-implemented method for the automatic detection of anatomical sites according to claim 1, wherein perform slice-level analyses on 2D axial slices of the pre-processed transformed images to detect the presence of the head and neck region using dimensional measurement thresholds based on human anatomy comprises:
   measure left-right dimension of the body mask on each axial slice after performing morphological erosion and determining if each of the axial slices have the head and neck region based on the accepted threshold configured from normal human anatomy; and
   employ the determined top and bottom 2D axial slices containing the head and neck region to measure the length of the head and neck region and comparing against the acceptable head and neck length threshold.

6. The computer-implemented method for the automatic detection of anatomical sites according to claim 1, wherein calculate the lung ratios on the 2D axial slices to determine if the lung mask are present in the axial slices comprises:
   define lung mask as the region with intensity lower than a certain threshold; and
   calculate lung mask to the body mask ratio on the axial slices to determine the presence of lung mask.

7. The computer-implemented method for the automatic detection of anatomical sites according to claim 1, wherein determine the presence of pelvis region on the pre-processed transformed images with no lung mask present by conducting 2D connectivity analysis on the 2D axial slices comprises:
perform slice-level 2D connectivity analysis on the axial slices from top of the body to the bottom to detect human leg by checking if morphological erosion outputs two distinct regions of roughly the same area.

8. The computer-implemented method for the automatic detection of anatomical sites according to claim 1, wherein differentiate detected pelvis regions as either male pelvis or female pelvis regions based on human anatomy comprises:
differentiate male pelvis from female pelvis regions by using patient's sex information; and
perform heavy morphological erosion to determine the presence of male genitalia for male pelvis.

9. An apparatus for the automatic detection of anatomical sites, comprising:
one or more processors;
a display; and
a non-transitory computer readable memory storing instructions executable by the one or more processors, wherein the instructions comprising:
receive 3D images obtained by a CT or an MRI system;
transform the received 3D images to the DICOM standard patient-based coordinate system;
pre-process the transformed images to normalize intensity values based on the received 3D images obtained by the CT or MRI system;
perform image segmentation on the pre-processed transformed images to obtain the body mask;
crop the pre-processed transformed images to remove excess areas outside the segmented body mask;
wherein anatomical sites consisting of head and neck, thorax, abdomen, male pelvis and female pelvis;
wherein the step of detecting the anatomical sites comprises:
create an empty list;
perform slice-level analyses on 2D axial slices of the pre-processed transformed images to detect the presence of the head and neck region using dimensional measurement thresholds based on human anatomy;
add the head and neck region in the list,
if the head and neck region is present;
perform image segmentation on the pre-processed transformed images to obtain lung mask;
calculate lung ratios on the 2D axial slices to determine if the lung mask are present in the axial slices;
determine whether the pre-processed transformed images with lung mask present includes at least one of the thoracic region, abdomen region or at least one of the combination thereof;
verify presence of neck region to determine the presence of thoracic region or the abdomen region;
determine the presence of both the thoracic region and the abdomen region,
if the thoracic region is present and the field-of-view of the pre-processed transformed images in the axial direction is large enough to cover both the thoracic and abdomen regions;
add the thoracic region or the abdomen region or both in the list,
if the thoracic region or the abdomen region or both are present;
determine the presence of pelvis region on the pre-processed transformed images with lung mask present;
determine the presence of pelvis region on the pre-processed transformed images with no lung mask present by conducting 2D connectivity analysis on the 2D axial slices;
differentiate detected pelvis region as either male pelvis or female pelvis region based on human anatomy;
add male pelvis or female pelvis region in the list,
if the pelvis region is present; and
output the list of all the detected anatomical sites.

10. The apparatus for the automatic detection of anatomical sites according to claim 9, wherein the instructions comprising:
transform the received 3D images to be sorted from superior to inferior in the axial direction, right to left in the sagittal direction, and anterior to posterior in the coronal direction.

11. The apparatus for the automatic detection of anatomical sites according to claim 9, wherein the instructions comprising:
receive the 3D images information includes pixel spacing, slice thickness, matrix size, and patient's sex;
apply lower and upper thresholds on CT image Hounsfield unit (HU) intensities; and
apply lower and upper thresholds on MRI image intensities using the image intensity percentiles.

12. The apparatus for the automatic detection of anatomical sites according to claim 9, wherein the instructions comprising:
apply threshold to image intensity;
perform 3D connectivity analysis to find 3D connected region after applying threshold to image intensity; and
fill holes to further improve the body mask segmentation.

13. The apparatus for the automatic detection of anatomical sites according to claim 9, wherein the instructions comprising:
measure left-right dimension of the body mask on each axial slice after performing morphological erosion and determining if each of the axial slices have the head and neck region based on the accepted threshold configured from normal human anatomy; and
employ the determined top and bottom 2D axial slices containing the head and neck region to measure the length of the head and neck region and comparing against the acceptable head and neck length threshold.

14. The apparatus for the automatic detection of anatomical sites according to claim 9, wherein the instructions comprising:
define lung mask as the region with intensity lower than a certain threshold; and
calculate lung mask to the body mask ratio on the axial slices to determine the presence of lung mask.

15. The apparatus for the automatic detection of anatomical sites according to claim 9, wherein the instructions comprising:
perform slice-level 2D connectivity analysis on the axial slices from top of the body to the bottom to detect human leg by checking if morphological erosion outputs two distinct regions of roughly the same area.

16. The apparatus for the automatic detection of anatomical sites according to claim 9, wherein the instructions comprising:
differentiate male pelvis from female pelvis regions by using patient's sex information; and
perform heavy morphological erosion to determine the presence of male genitalia for male pelvis.

17. A non-transitory computer-readable storage medium having stored therein instructions that, when executed by one or more processors of an apparatus causing the apparatus to perform comprising:
- receive 3D images obtained by a CT or an MRI system;
- transform the received 3D images to the DICOM standard patient-based coordinate system;
- pre-process the transformed images to normalize intensity values based on the received 3D images obtained by the CT or MRI system;
- perform image segmentation on the pre-processed transformed images to obtain the body mask;
- crop the pre-processed transformed images to remove excess areas outside the segmented body mask;
- wherein anatomical sites consisting of head and neck, thorax, abdomen, male pelvis and female pelvis;
- wherein the step of detecting the anatomical sites comprises:
- create an empty list;
- perform slice-level analyses on 2D axial slices of the pre-processed transformed images to detect the presence of the head and neck region using dimensional measurement thresholds based on human anatomy;
- add the head and neck region in the list, if the head and neck region is present;
- perform image segmentation on the pre-processed transformed images to obtain lung mask;
- calculate lung ratios on the 2D axial slices to determine if the lung mask are present in the axial slices;
- determine whether the pre-processed transformed images with lung mask present includes at least one of the thoracic region, abdomen region or at least one of the combination thereof;
- verify presence of neck region to determine the presence of thoracic region or the abdomen region;
- determine the presence of both of the thoracic region and the abdomen region,
- if the thoracic region is present and the field-of-view of the pre-processed transformed images in the axial direction is large enough to cover both the thoracic and abdomen regions;
- add the thoracic region or the abdomen region or both in the list,
- if the thoracic region or the abdomen region or both are present;
- determine the presence of pelvis region on the pre-processed transformed images with lung mask present;
- determine the presence of pelvis region on the pre-processed transformed images with no lung mask present by conducting 2D connectivity analysis on the 2D axial slices;
- differentiate detected pelvis region as either male pelvis or female pelvis region based on human anatomy;
- add male pelvis or female pelvis region in the list, if pelvis region is present; and
- output the list of all the detected anatomical sites.

* * * * *